United States Patent [19]

MacLaury

[11] 4,180,685
[45] Dec. 25, 1979

[54] DEHYDROCHLORINATION OF A DIHYDROXYDIPHENYL TRICHLOROETHANE

[75] Inventor: Michael R. MacLaury, Rexford, N.Y.

[73] Assignee: General Electric Company, Schenectady, N.Y.

[21] Appl. No.: 4,050

[22] Filed: Jan. 17, 1979

[51] Int. Cl.$^2$ .............................................. C07C 37/00
[52] U.S. Cl. .................................................... 568/726
[58] Field of Search ......................................... 568/726

[56] References Cited

U.S. PATENT DOCUMENTS

| 4,097,538 | 6/1978 | Factor et al. | 568/726 |
| 4,117,018 | 9/1978 | Cleveland et al. | 568/726 |

FOREIGN PATENT DOCUMENTS 144765 9/1975 Poland.

OTHER PUBLICATIONS

McCelland et al., "J. Chem. Soc. Perk. II", pp. 1818–1822, 308 (1972).
Holysz, "J. Chem. Soc.", 75: 4432–4437, (1953).
Porejko et al., "Polimery", 13(2), 55 (1968).
Sobicaewski et al., "On the Stabilty of Polycarbonates from Chorobrophenols", Inst. for Plastics, Warsaw, Poland, 10/26/67.
Dubkowski, et al., "Syn. of Polycarbonates by Interfacial Methods", Ibid 428–431, (1970).
Wielgosz et al., "Polimery-Tworzywa Wielkoczastecz", 1971, 495–500.
Wielgosz et al., "Polimery", 17,76 (1972).
Trojna et al., "Chem. Listy", 51, 752–755 (1957).
Hiwacher, "J. Org. Chem.", 24, 1949–1951, (1959).
Grummat et al., "Org. Syn.", 26, 21 (1946).
Lord, "J. Chem. Soc.", 1657 (1948).

*Primary Examiner*—Norman Morgenstern
*Attorney, Agent, or Firm*—Joseph T. Cohen; Leo I. MaLossi

[57] ABSTRACT

1,1,1-trichloro-2,2-bis(4-hydroxyphenyl)ethane can be dehydrohalogenated to 1,1-dichloro-2,2-bis(4-hydroxyphenyl) ethylene by treating the former with a dehydrochlorinating agent consisting of liquid methyl amine.

6 Claims, No Drawings

DEHYDROCHLORINATION OF A DIHYDROXYDIPHENYL TRICHLOROETHANE

This invention is concerned with a process for dehydrohalogenating a dihydroxydiphenyl trichloroethane. More particularly, the invention is concerned with a process for obtaining in good yield and purity the compound 1,1-dichloro-2,2-bis(4-hydroxyphenyl)ethylene (hereinafter referred to as "dichloride") having the formula

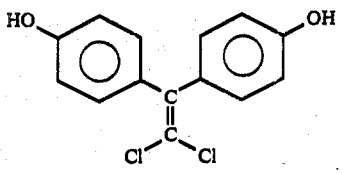

by treating 1,1,1-trichloro-2,2-bis(4-hydroxyphenyl)ethane (hereinafter referred to as "trichloride") having the formula

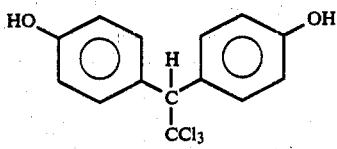

with liquid methyl amine in the substantial absence of a solvent.

The dehydrochlorination of the aforesaid trichloride to the dichloride is reported in numerous publications. M. Trojna and J. Hubacek, Chem. Listy 51, 752 (1957) [also described in Chemical Abstracts 51, 11297a (1957)] treated the trichloride with a large molar excess of aqueous sodium hydroxide at elevated temperatures to obtain a 35% yield of the dichloride. Hubacher, in J. Org. Chem. 24, 1949 (1959), reported an improved dehydrochlorination procedure using 6 mol equivalents of KOH in methanol to give a 74% yield of the dichloride that was pale yellow in color.

S. Porejko and Z. Wielgosz, in the publication Polimery 13, 55 (1968) improved the dehydrochlorination technique by lowering the reaction temperature and using 15 mol equivalents of KOH in methanol to give a 90% yield of the dichloride. The Polish patent 144,765 of Wielgosz, Krajewski, and Rawski, published September 8, 1975, effected dehydrochlorination using KOH in methanol at about 40° C. for 3 hours, followed by heating to reflux. Neutralization with acid and crystallization from water afforded a 91% yield of the dichloride. Evaluation of this latter procedure revealed that the dichloride obtained had significant amounts of impurities and was highly colored rather than white.

K. A. Lord in J. Chem. Soc., 1657 (1948) describes the dehydrochlorination of DDT having the formula

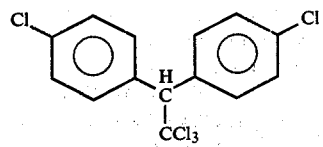

using methyl amine in the form of a dilute solution of the amine in aqueous dioxane or other solvents such as ethylene glycol monoethyl ether and benzene. There is no indication expressed or implied that the methyl amine was used to dehydrochlorinate the bisphenol of formula II nor that the dehydrochlorination of the DDT was carried out in the absence of a solvent. According to Lord's reaction conditions, these reactions were very slow as evidenced by the fact that the dehydrochlorination reaction of DDT with methyl amine was about 89% complete after 3.9 days. It would be expected that the hydroxyl group on the bisphenol of formula II would tend to markedly deactivate the dehydrochlorination reaction. Furthermore, there is nothing in the Lord reference which would indicate that the dehydrochlorination of the bisphenol of formula II with methyl amine in the absence of a solvent could proceed even at close to room temperature in a rapid manner with close to quantitative yields. Stated alternatively, with the Lord reference before him, a person skilled in the art could be discouraged from attempting the dehydrochlorination of the bisphenol of formula II because of the extremely slow reaction rate and because of the expectation that increasing temperature and concentration of amine would lead to low yields of the desired chloroethylene compound of formula I.

U.S. Pat. Nos. 4,097,538, issued June 27, 1978 and assigned to the same assignee as the present invention, describes the dehydrochlorination of the trichloroethane derivative with liquid ammonia to give the dichloride of formula I. The use of ammonia for dehydrochlorination has many advantages as are carefully brought out in this patent. One of the main features of using the liquid ammonia for dehydrohalogenation are the low amounts of impurities which are obtained as a result of carrying out the dehydrohalogenation step. One disadvantage in using liquid ammonia is the fact that there is a minimum temperature and pressure which is required to be maintained in order to ensure a viable rate of reaction. It would accordingly be desirable to find a more reactive base for removing the HCl in forming the dichloride.

I have now discovered that liquid methyl amine in the absence of any solvent can be used to dehydrochlorinate the trichloride to the dichloride and in so doing, several advantages are derived over previously described procedures. In the first place, no additional solvent of any kind is required and indeed is preferred; the methyl amine acts as both the reactant and the solvent medium. In order to separate the dichloride from the reaction solution, one only needs to heat the methyl amine at a relatively low temperature to remove it from the reaction mixture for further use. Moreover, the dichloride obtained by this procedure, after the by-product methyl-amine hydrochloride has been removed, can readily be crystallized from a slightly acidic methanol-water solution in exceptionally good yields. What is equally significant is the fact that by using methyl amine, dehydrochlorination can be carried out at lower temperatures and pressures than when using, for example, liquid ammonia for the same purpose as described in the aforesaid U.S. Pat. No. 4,097,538. This advantage is accomplished with a decrease in the reaction time as compared to the use of ammonia under similar conditions.

As an example of the advantage of methyl amine over ammonia, and the speed with which the dehydrochlorination reaction can be carried out under much milder conditions of temperature and pressure, it is found that, for example, at 30° C. and only 49 psi the dehydrochlorination reaction is complete in 7 hours, while at 50° C. and about 100 psi the reaction is complete in a little more than 2½ hours. At temperatures of 100° C., the reaction is complete in 20 minutes, while still giving high purity dichloride. In contrast, the ammonia dehydrochlorination reaction is considerably slower at any given temperature, for instance, the methyl amine having a 13 minute half-life versus a 40 minute half-life for liquid ammonia both measured at 50° C. In addition, much less pressure is required to contain the reaction solution using the methyl amine as contrasted to the use of the liquid ammonia; for example, at 50° C. about 100 psi was required for the methyl amine, while about 300 psi was required for the liquid ammonia. With these advantages in the use of liquid methyl amine, the fact that a somewhat higher amount of impurities is obtained with the methyl amine is more than offset by the increased rate of reaction and the lower temperatures and pressures capable of being used with the methyl amine.

I am aware that the aforesaid U.S. Pat. No. 4,097,538 discusses the possibility of using methyl amine for dehydrohalogenation. However, in the context in which it is disclosed and discussed in this patent, it would appear that methyl amine would be an undesirable means for dehydrochlorination. I have unexpectedly discovered that contrary to the belief existing at the time of filing the aforesaid U.S. Pat. No. 4,097,538, liquid methyl amine when further examined was found to have the highly desirable attributes described above which were entirely unappreciated earlier and which made feasible the use of methyl amine and pointed to more favorable results than when ammonia was used.

Although a large molar excess of methyl amine is used to serve both as a reactant and as a solvent medium, the dehydrochlorination only uses 1 mol of methyl amine per mol of trichloride, and at the end of the reaction the unused methyl amine can be easily recovered by distillation (boiling point −6.3° C.). Thus, large amounts of acid are not needed to neutralize the reaction mixture as is required in the KOH/methanol procedure.

In the discussion above, contaminant impurities have been referred to and specifically these impurities or contaminants comprise one or both of the following:

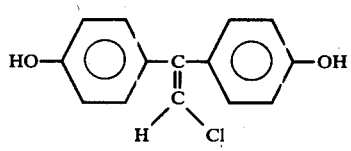
("Monochloro compound")    III

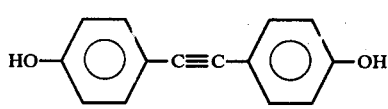
("Acetylene compound")    IV

One of the uses to which the dichloride of the present invention can be put is in the formation of polycarbonate resins comprising the following recurring unit:

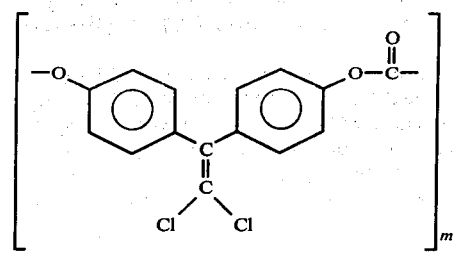

where m is a whole number greater than 1. Such polymers are more particularly described in Polish Pat. No. 48,893, issued Dec. 12, 1964. It has been found that, because the dichloride prepared in accordance with the description in the aforesaid Polish Pat. No. 48,893 is not of adequate purity (as established by the number and amount of contaminants and by the color), polycarbonates made by the reaction of the dichloride and a phosgenating precursor, such as phosgene, diphenyl carbonate, etc., have impact values which are lower than desirable or might even be expected from the usual polycarbonates, for instance, those made from a precursor phosgenating agent and bisphenol-A. As shown in U.S. Pat. No. 4,117,018 issued Sept. 26, 1978, and assigned to the same assignee as the present invention, marked and unexpected improvements in impact characteristics of polycarbonate resins can be realized if highly purified dichloride is employed for the purpose. It is for this reason that the present invention, providing for purer monomer dichloride, permits the attainment of high impact polymers.

As used hereinafter, the expression "substantially pure," when referring to dichloride, will signify a dichloride having an absorbance value of less than 0.3, as shown by measuring the absorbance of a methanol solution of the dichloride (2.50 gm/50 ml in a 10 cm cell) using a Carey 14 recording spectrophotometer with light at 425 nm.

A Waters Model 244 liquid chromatograph is used, equipped with a Model U6K injector, a $\mu C_{18}$ Bondapak column, a Model 440 detector equipped with a 1 cm cell and operated at 280 nm set at 0.1 AUFS and a 10 millivolt Houston Instrument Omniscribe recorder with a chart speed of 0.25 centimeter per minute. Ten microliters of a 10% (wt./vol.) methanol solution of the dichloride is injected into the column and it is eluted at 2 ml per minute, where the solvent mixture is programmed linearly over a 1 hour period from an initial composition of 40% methanol and 60% water to a final composition of 100% methanol.

In accordance with my invention, the dehydrochlorination of the trichloride can be achieved by charging the trichloride to a pressure reactor together with the liquid methyl amine, and thereafter heating the pressure reactor at temperatures ranging from 15° to 100° C., and preferably from 25° to 75° C., for times ranging from about 20 minutes to 6 hours or more to effect the dehydrohalogenation. Thereafter, the formed dichloride can be removed from the liquid methyl amine solvent by first allowing the methyl amine to evaporate (either at atmospheric pressure and/or by vacuum), collecting the crude product, and then washing the crude product with water, thereby removing the methyl amine hydrochloride from the dichloride. If further purification is desired, the dichloride can then be recrystallized from a methanol-water mixture whose pH has been adjusted to 3-5 in which any impurities present in the dichloride are soluble.

The amount of liquid methyl amine used with regard to the trichloride undergoing dehydrohalogenation can be varied widely. At least one mol of the methyl amine should be used per mol of trichloride. However, for optimum results, in order to attain the objective of using the methyl amine both as a reactant and as a solvent medium, I have found that molar concentrations ranging from about 3 to 20 or more mols of methyl amine per mol of the trichloride are advantageously employed. Because the trichloride is more soluble in the liquid methyl amine than in the liquid ammonia, normally less methyl amine can be used with obvious advantages to optimum use of pressure equipment. It is evident that the size of the pressure reactor will in many instances dictate the molar concentrations of the methyl amine and the trichloride.

Depending on the temperatures and the amount of methyl amine present in the pressure reactor, pressures ranging from 50 psi to 200 psi or more can advantageously be employed without materially affecting the results. The temperature used will depend on the type and size of the pressure reactor employed, the molar concentrations of the methyl amine and the trichloride, etc. The reaction using the methyl amine can be run at a relatively low temperature with little or no significant increase in impurities; also total reaction times of shorter duration are possible than with other methods for dehydrohalogenation. Thus, it has been found at about 60° C., the dehydrohalogenation reaction is complete in one hour compared to three hours for the KOH/methanol process described in the above-identified Polish Pat. No. 144,765.

Under the pressure conditions employed in the practice of my invention, temperature is an important function in the attainment of as pure a dichloride as possible free of any by-products or of any of the starting trichloride. Thus, as one proceeds from around room temperature (about 20°-30° C.) to about 100° C., one will find that with the use of reasonable times of reaction, for instance, about 30-90 minutes at the upper end of the temperature range, substantially all of the trichloride is converted to the dichloride in a fairly pure state and no detectable amount of trichloride is present in the final product.

As pointed out above, the reaction between the liquid methyl amine and the trichloride should avoid the use of any solvent. To do otherwise would defeat the whole purpose of my discovery.

Contrary to what might be expected, secondary and tertiary amines were very slow in effecting the dehydrohalogenation and, in addition, they caused the formation of large amounts of side products and highly colored impurities.

In order that those skilled in the art may better understand how the present invention may be practiced, the following examples are given by way of illustration and not by way of limitation. Unless otherwise indicated, all parts are by weight.

EXAMPLE 1

About 10 grams of the trichloride of formula II were dissolved in about 20 ml liquid methyl amine (condensed at −78° C.) in a pressure reaction vessel. The reaction vessel immersed in a constant temperature bath was closed and heated at 26° C. for 16 hours while the mixture inside the pressure vessel was continuously agitated. At this point the reaction was essentially complete. The pressure vessel was opened and the excess liquid methyl amine allowed to evaporate; final removal of the methyl amine was accomplished by the use of vacuum. The solid product was dissolved in 80% aqueous methanol (5% solids), acidified to a pH of 3-5 with concentrated HCl, and diluted with water to form a 50% aqueous methanol solution. This solution was heated to about 75° to 80° C. and then slowly cooled to room temperature (about 25° C.) to give a 98% yield of the desired product of formula I in the form of white needles.

The aforesaid purified product was examined for absorbance value in the manner described previously, and found to have an absorbance of 0.105, while the same product prepared using liquid ammonia but at a temperature of about 100° C. would have an absorbance value of about 0.08.

The purified reaction product was also analyzed in the manner described above for the presence of the monochloro compound of formula III and the acetylene compound of formula IV. It was found that the above-described compound of formula I had approximately 2000 parts of the monochloro compound per million parts of product, as contrasted to 150 parts of the monochloro compound per million parts of product using the ammonia method of dehydrochlorination but conducting the reaction at a temperature of 100° C. When the reaction using the methyl amine was carried out at about 100° C., 16,000 parts of the monochloro compound per million parts of dichloride were found. It has been determined that this extra amount of monochloro compound (2000 parts) present in the product using the methyl amine process is tolerable and does not significantly affect the properties of polycarbonate resins using the dichloride for making the latter.

The purified product of Example 1 was also analyzed for the presence of the acetylene compound of formula IV and was found to contain 5 parts of the acetylene compound per million parts of product. When the reaction with the methyl amine was conducted at about 100° C. for about 6 minutes, an almost quantitative yield of dichloride was obtained and the product contained 80 parts of the acetylene compound per million parts of product. In contrast to this, the dichloride made by the ammonia process was essentially free of the acetylene compound, again when the reaction was conducted at 100° C. As pointed out above, this difference in the amounts of the acetylene compound using the methyl amine versus the ammonia was insignificant as far as the properties of polycarbonate resins were concerned made from such monomers.

To demonstrate the exclusive position which methyl amine occupies as a dehydrochlorinating agent for converting the trichloride to the dichloride as compared to, for instance, other very similar amines, particularly ethyl amine and dimethyl amine, the following example shows the results of using these three amines for dehydrochlorination purposes.

EXAMPLE 2

In this example, methyl amine, ethyl amine, and dimethyl amine were used similarly as in Example 1 but employing a reaction temperature of 50° C. and a reaction time of 16 hours. The work-up of the product, including isolation and crystallization, was essentially the same as in Example 1. The following Table I shows the results of analyzing the products obtained in each instance.

TABLE I

| Amine | Monochloride *(ppm) | Acetylene Compound *(ppm) | **t½ (min.) |
|---|---|---|---|
| CH$_3$NH$_2$ | 6800 | 20 | 12 |
| C$_2$H$_5$NH$_2$ | 19800 | 180 | 76 |
| (CH$_3$)$_2$NH$_2$ | 2000 | not measurable | 102 |
| NH$_3$ | 2000 | 200 | 48 |

*Parts impurity/million parts dichloride.
**Half-life of reaction-the smaller the number, the greater the rate of reaction.

In order to establish the criticality of using the methyl amine in a nonsolvent, and nonaqueous medium, the following work was carried out reproducing the efforts of K. A. Lord in his aforementioned article for dehydrochlorinating DDT and applying the same set of conditions to where a solvent and an aqueous medium was used in combination with methyl amine for the dehydrochlorination of the trichloroethane of formula II.

EXAMPLE 3A 3.50 grams (0.0099 mol) DDT was suspended in 5 ml dioxane and the mixture warmed to around 59°-60° C., at which temperature it became homogeneous. 1 ml of 3.5 molar aqueous methyl amine (0.0035 mol) was added to the solution. The sample mixture was stirred for 4.25 hours and thereafter analyzed by gas chromatography. This revealed that 33.5% of the DDT had been converted to the dehydrochlorinated product, having the formula

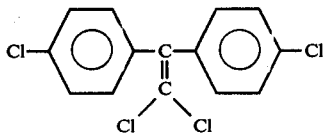

This corresponds to 95.7% complete reaction based on the mols of methyl amine employed.

EXAMPLE 3B

Employing the identical conditions as in Example 3A, 3.2 grams (0.01 mol) of the trichloride of formula II was suspended in 5 ml dioxane and again warmed to 59°-60° C. To the trichloroethane solution in dioxane was added 1 ml of a 3.5 molar aqueous, methyl amine solution (0.0035 mol). After about 15 minutes of stirring, the reaction mixture became homogeneous. The mixture of ingredients was heated with stirring for 4.25 hours and thereafter was analyzed by gas chromatography which showed that only 2.9 mol % of the dichloride of formula I had been formed; this corresponds to 8.3% reaction based on the methyl amine used. After further stirring this mixture for a total of 12.5 hours, the mixture became very dark brown and only 10 mol % of the dichloride of formula I was obtained which represented a 28.6% reaction based on the methyl amine employed.

In view of the above results of Examples 3A and 3B, it is evident that if one were to follow the teachings of Lord, one could properly conclude that methyl amine as a dehydrohalogenating agent for the trichloride of formula II would be unacceptable because it proceeded so slowly and afforded highly colored impurities. The fact that I found that methyl amine, in the absence of any solvent or aqueous medium, did proceed rapidly to give high yields of the dichloride in relatively short periods of time was unexpected.

The dichloride obtained in accordance with the present invention has many uses. One of the more important uses to which this composition may be put is as an intermediate in the preparation of heat-resistant polyester resins which have many uses. For instance, the dichloride can be reacted with phthalic acid esters or certain phthalic acids themselves, such as dimethyl terephthalate, terephthalic acid, isophthalic acid, etc., to make polyester resins. An important use for the dichloride is in the preparation of flame and heat resistant polycarbonate resins by reacting the dichloride with precursor carbonating agents, such as phosgene, diphenyl carbonate, etc.

The polymeric compositions derived from the reaction of the dichloride here described have many applications. These polymeric compositions may be used to form fibers, films, or molded products. Thus, either by extrusion from melt or by depositing from solution, fibers derived from these polymeric compositions may be formed and used in the preparation of various textile materials designed for clothing and similar applications.

Various fillers may be incorporated in the polymeric compositions prior to molding thereof. Among such fillers may be mentioned glass fibers, carbon black, titanium dioxide, silica, mica, bentonite, etc. Molded products derived from such a mixture of ingredients can be used as gears, handles for cooking utensils, etc. The incorporation of abrasive particles such as carborundum, diamond powder, etc., makes molded products derived from such polymeric compositions useful as grinding wheels, etc. The addition of carbon, silicon carbide, powdered metal, conducting oxides, etc., to the polymeric compositions results in the so-called resistance or semiconducting paints which have many useful applications.

What I claim as new and desire to secure by Letters Patent of the United States is:

1. The process for dehydrohalogenating 1,1,1-trichloro-2,2-bis(4-hydroxyphenyl)ethane to form 1,1-dichloro-2,2-bis(4-hydroxyphenyl)ethylene of the formula

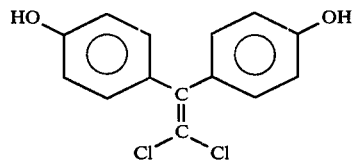

which process comprises treating the aforesaid trichloroethane with liquid methyl amine substantially free of solvent.

2. The process as in claim 1 wherein the amount of methyl amine used is stoichiometrically in excess of the trichloroethane.

3. The process as in claim 1 wherein the dehydrohalogenation step is carried out under superatmospheric pressure and at a temperature of from about 15° to 100° C.

4. The process for making a dichloroethylene of the formula

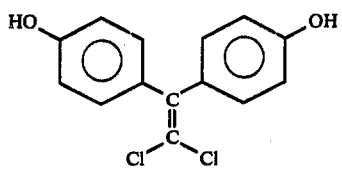

which comprises reacting at superatmospheric pressure a trichloroethane of the formula

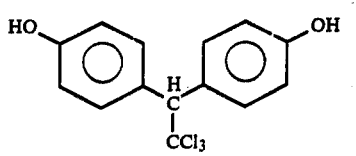

with methyl amine substantially free of solvent and in a molar excess over the molar concentration of the aforesaid trichloroethane and thereafter isolating the formed dichlorothylene.

5. The process as in claim 4 wherein the formed dichloride is treated with a methanol/water mixture to remove residual impurities.

6. The process as in claim 5 wherein the treatment with the methanol/water mixture is at a pH between 3 to 5.

* * * * *